United States Patent [19]

Afilani

[11] Patent Number: 5,748,088
[45] Date of Patent: May 5, 1998

[54] DEVICE AND METHOD USING DIELECTROKINESIS TO LOCATE ENTITIES

[76] Inventor: Thomas L. Afilani, Electroscopes, 2401 Reach Rd., Suite 301, Williamsport, Pa. 17701

[21] Appl. No.: 758,248

[22] Filed: Nov. 27, 1996

[51] Int. Cl.[6] ........................................... G08B 23/00
[52] U.S. Cl. ........................ 340/573; 340/562; 307/116; 324/457
[58] Field of Search .................... 340/573, 572, 340/568, 561, 562, 540, 541; 307/116; 324/457

[56] References Cited

U.S. PATENT DOCUMENTS

| | | | |
|---|---|---|---|
| 3,771,152 | 11/1973 | Dettling et al. | 340/562 |
| 3,836,899 | 9/1974 | Duvall et al. | 340/562 |
| 3,898,472 | 8/1975 | Long | 340/562 |
| 4,316,180 | 2/1982 | LeVert | 340/562 |
| 4,320,766 | 3/1982 | Alihanka et al. | 340/562 |
| 4,339,709 | 7/1982 | Brihier | 324/457 |
| 5,019,804 | 5/1991 | Fraden | 340/562 |
| 5,436,613 | 7/1995 | Ghosh et al. | 340/573 |
| 5,446,391 | 8/1995 | Aoki et al. | 340/562 |

FOREIGN PATENT DOCUMENTS 1-113692   5/1989   Japan ......................... 324/71.1

*Primary Examiner*—Thomas Mullen
*Assistant Examiner*—Nina Tong
*Attorney, Agent, or Firm*—Nixon & Vanderhye P.C.

[57] ABSTRACT

The dielectrophoretic force caused by the non-uniform electric field squared spatial gradient three-dimensional pattern uniquely exhibited by a predetermined type of entity can be detected by locator device. A human operator holds the device in hand to thereby electrically connect to the human operator. The human operator's naturally occurring very low electrical decay time constant is increased through electronic circuitry externally connected to the device. The device is held in a balanced horizontal state, and the operator scans the device in a constant uniform motion back and forth. An antenna extends from the front of the device, and both are acted on by the dielectrophoretic force. This force results in a subsequent resulting torque, acceleration, vibration or any other measurable quantifiable manifestation of the force about the handle's pivot line hence driving the device and its antenna toward the direction and position of any entities of the predetermined type that are within range.

30 Claims, 7 Drawing Sheets

DEVICE AND METHOD USING DIELECTROKINESIS TO LOCATE ENTITIES

BACKGROUND OF THE INVENTION

1. Field of the Invention

The present invention relates to methods and apparatus for locating various entities, including human beings and animals, by observing and detecting a force and subsequent resulting torque, acceleration, vibration or other measurable, quantifiable manifestation of the force created by the non-uniform three-dimensional electric field spatial gradient pattern exhibited uniquely by the entity and being detected by the device of the present invention as used by the device's human operator.

2. Description of the Prior Art

The detection of visually obscured entities, specifically human beings, has many uses in the following areas: fire-fighting and rescue search operations; law enforcement operations; military operations; etc. While prior art devices are known that detect humans, animals and other materials, some by measuring changes in an electrostatic field, none of the operable prior art devices uses the force resulting from the non-uniform electric field squared spatial gradient three-dimensional pattern exhibited uniquely by an entity to indicate the precise location and direction of the subject entity relative to the device's operator. By using an electrokinetic effect, dielectrophoresis, that induces a force and subsequent resulting torque on an antenna and other component parts of the device, the present invention gives a rapid directional location indication of the subject entity. A meter can also be provided to indicate the direction of strongest non-uniform electric field squared spatial gradient signal strength for those situations where the dielectrophoretic force and subsequent resulting torque, acceleration, vibration or any other measurable quantifiable manifestation of the force is extremely small and difficult to detect. It should be noted that while the present invention works for many different types of entities, a primary use of the present invention is to locate human beings, irrespective of the presence or absence of obscuring material structures (walls, trees, earthen mounds, etc.), of rfi and emi interference signals, of adverse weather conditions, and of day or night visibility conditions.

U.S. Pat. No. 3,771,152, (Dettling et al.) discloses an intrusion detector wherein changes in an electrostatic field caused by an intruder generate a detection signal. No directional information is derived. U.S. Pat. No. 4,316,180 (LeVert) discloses a directional detector that locates an intruder (human) by measuring changes in a local electrostatic field. Two coils are used to differentiate between front and rear sides of the device. No specific actual directional indication is given. U.S. Pat. No. 5,3436,613 (Ghosh et al.) measures a dissipation of an electrical field to determine that biological tissue, as opposed to conductors or insulators, has penetrated the field. Japanese Patent No. 113692 discloses a person detecting device that measures the difference in electrostatic capacity.

None of the above inventions and patents, taken either singly or in combination, is seen to describe the instant invention as claimed.

SUMMARY OF THE INVENTION

The present invention detects the presence of various entities using an electrokinetic effect known as dielectrophoresis. As discussed above, a primary use of the present invention is detecting and locating human beings that are obscured from sight. The electrokinetic effect used by the present invention, dielectrophoresis, is one of five known electrokinetic effects, (the other four being electrophoresis, electro-osmosis, Dorn effect, and streaming potential), and describes the forces affecting the mechanical behavior of initially neutral matter that is dielectrically polarized by induction via spatially non-uniform electric fields. The spatial non-uniformity of an electric field can be measured by the spatial gradient of the electric field. The dielectrophoresis force depends non-linearly upon several factors, including the dielectric polarizibility of the surrounding medium (air plus any intervening walls, trees, etc.), the dielectric polarizibility and geometry of the initially neutral matter (device's antenna and other component parts of the device), and the spatial gradient of the square of the human target's local electric field distribution as detected at the device's antenna and other component parts. The spatial gradient is measured by the dielectrophoresis force produced by the induced polarization charge on the device's antenna and other component parts, and this force is a constant direction seeking force always pointing (or trying to point) the device's antenna and other component parts toward the maximum in the three-dimensional non-uniform electric field squared spatial gradient pattern uniquely exhibited by a predetermined entity type.

This constant direction seeking force is highly variable in magnitude as a function of the angular position and radial position of the entity-to-be-located (like a human target) with respect to the device's antenna and other component parts of the device, and upon the effective dielectric polarizibilities of the intervening medium (like air) and of the materials used in the device's antenna and other component parts. The following equations define the dielectrophoresis forces wherein equation 1 shows the force for spherical initially neutral objects (spherical antenna and the device's other component parts), and equation 2 shows the force for cylindrical initially neutral objects (cylindrical antenna and the device's other component parts).

$$F=3/2(4/3(\pi a^3)) \epsilon_0 K_1(K_2-K_1)/(K_2+2K_1)\nabla|E_0|^2$$

Equation 1

$$F=(\pi a^2)(L)\epsilon_0 K_1(K_2-K_1)/(K_2+K_1)\nabla|E_0|^2$$

Equation 2

Where:

F is the dielectric force vector detected by the antenna and the device's other component parts;

a is the radius of the sphere or cylinder;

L is the length of the cylinder;

$\epsilon_0$ is the permittivity constant of free space;

$K_2$ is the dielectric constant of the material in the sphere or cylinder;

$K_1$ is the dielectric constant of fluid or gas, (air) surrounding both the entity and the antenna and the device's other component parts;

$E_0$ is the electric field produced by the entity as detected by the antenna and the device's other component parts; and $\nabla$ is the spatial gradient mathematical operator.

It should be noted that the term "antenna" as used in this context includes, (in a very real sense), all of the components present in the device of the present invention. To this extent, the dielectric constant of the materials that make up the locator of the present invention all determine the overall value of $K_2$ in the above equations. These materials are not arranged in a uniform spherical or cylindrical shape, and therefore the exact value of $K_2$ is difficult to determine. In a practical sense, experimentation has shown (and is continuing to show) the types and placement of dielectric materials needed to produce maximum dielectrophoretic force and subsequent resulting torque, acceleration, vibration or any other measurable quantifiable manifestations of the force for precisely locating different types of entities. The following table lists some of the dielectric materials used in the locator ($K_2$ values) and/or surrounding (such as air, water, walls, etc.) the locator ($K_1$ values) and the dielectric constant for these materials.

| MATERIAL | DIELECTRIC CONSTANT |
|---|---|
| air | 1.0 |
| PVC | 3.0 |
| nylon | 4.0 |
| polyester | 5.5 |
| silicon | 12.0 |
| 2-propanol | 19.9 |
| water | 78.4 |
| n-maa | 191.3 |
| selenium | 1000 |
| $BaTiO_3$ | 4000 |
| $(CS_2)_n$ | 20,000 |
| metal | ∞ |

The above discussion and equations concerning dielectrophoresis provide a rational explanation of the operating principles of the present invention that is consistent with all empirical observations associated with the present invention. These operating principles involve using the above mentioned forces to point an antenna toward the maximum gradient of the local electric field, to thereby indicate the direction toward an unseen entity.

In accordance with the invention, an operator holds the locator device in hand, and through a handle, the locator device is electrically connected to the operator. The operator is partially electrically grounded (through the operator's feet), and thereby the individual human operator body's capacitance (C) and resistance (R) to true ground are connected electrically to the handle of the locator device. Ranges for individual human body's C have been measured as 100 pF to 400 pF and for individual human body's R have been measured as 0.03 KΩ to 1 MΩ. Thus, the generalized electrical parameter (the polarization charge pattern induced on the device by the electric field spatial gradient of the entity in this case, but also electric field, current and voltage) exponential decay time (=RC) constant range for the variety of human being bodies potentially acting as locator device operators is about 3 to 400µ seconds. This decay time constant is s greatly increased through an externally connected series resistor of up to 100 KΩ and parallel capacitor up to 0.01 mF, which results in an effective human operator's exponential decay time constant up to 1 to 10 seconds.

This enables dielectrophoretic forces caused by the induced polarization charges (bound, not free) pattern on the locator device's antenna and other component parts to be detected, replenished instantly and locked onto since the force is replenished faster than the induced polarization charge pattern on the device can decay away to true ground through the operator's body. This effect is called and is using the spatially self-correcting nature of the dielectrophoretic force (always pointing or trying to point to the maximum of an entity's electric field three-dimensional squared spatial gradient pattern).

The locator device is held in a balanced horizontal state, and the operator scans the locator device in a constant uniform motion back and forth. An antenna extends from the front of the locator device and is acted on by the aforementioned forces. These forces create a subsequent resulting torque around a well defined pivot line which tends to make the locator device's antenna and the device's other component parts point toward the maximum spatial gradient of the square of the non-uniform electric field uniquely exhibited by any "target" human beings or other predetermined entity type within the range of the locator device.

The effect creates a self-correcting action of the locator device when the human operator scans the device in a uniform motion to "lock onto" a target entity initially. The effect also creates an additional self-correcting action of the locator device to closely follow the radial and angular motions of an entity (to track and reacquire a target entity once the operator has initially locked onto a target entity). The self-correcting action of the locator device to reacquire a target occurs without any additional overt action on the part of the human operator, and the device thereby is operating independently of the human operator.

Four internal N-channel J-FETs (field effect transistors) are connected to the locator device's antenna and operate in their non-linear range to effectively change the antenna's length. Three of these FETs are arranged in modules that are equidistant from the antenna's longitudinal axis and are spaced 120 degrees apart. The fourth FET is arranged in a module below the axis and to the rear of the locator device. Three potentiometers are provided on the first three modules to adjust the current levels through the first three FETs and thereby tune the locator to point directly at a human being's body located at a precise known position as a reference target entity. The gain and frequency response of the fourth FET by virtue of the voltage pattern induced by the reference entity is adjusted by a six position switch connected to the base of an NPN transistor. By changing the frequency response of the locator device, the device is tuned to reject the higher frequency electromagnetic signals and noise from all external sources, including those sources associated with the human operator himself in order for the locator device to interact with and respond to only the three-dimensional non-uniform electric field squared spatial gradient pattern exhibited uniquely by a predetermined entity type.

While scanning the locator device in a constant uniform motion back and forth in front of a known entity (such as a human, if the target is a human being), the operator changes the six position switch until a maximum force and subsequent resulting torque is detected and used to "aim" the antenna and the device's other component parts toward the target entity. After selecting the setting of the six position switch, the operator adjusts the gain of the first three FETs until the locator device points or tries to point directly at the target entity. For different entities, different dielectric materials are used in the locator device's antenna and its other component parts. Examples of detectable entities include human beings, animals, metals, plastics and other materials. Continued research on the instrument has yielded positive results in the instrument's ability to be tailored both as a geometrical design and materials of construction to specifically detect a variety of different target entities.

Accordingly, it is an objective of the invention to provide an accurate method of locating the direction and position of a human being's body relative to the instrument's human operator.

It is another objective of the invention to provide an accurate method of locating the direction and position of a predetermined type of animal relative to the instrument's human operator.

It is a further objective of the invention to provide an accurate method of locating the direction and position of a predetermined type of material relative to the instrument's human operator.

It is an objective of the invention to provide improved elements and arrangements thereof in an apparatus for the purposes described which is inexpensive, dependable and fully effective in accomplishing its intended purposes.

These and other objectives of the present invention will become readily apparent upon further review of the following specification and drawings.

DETAILED DESCRIPTION OF THE PREFERRED EMBODIMENTS

Figure 1:
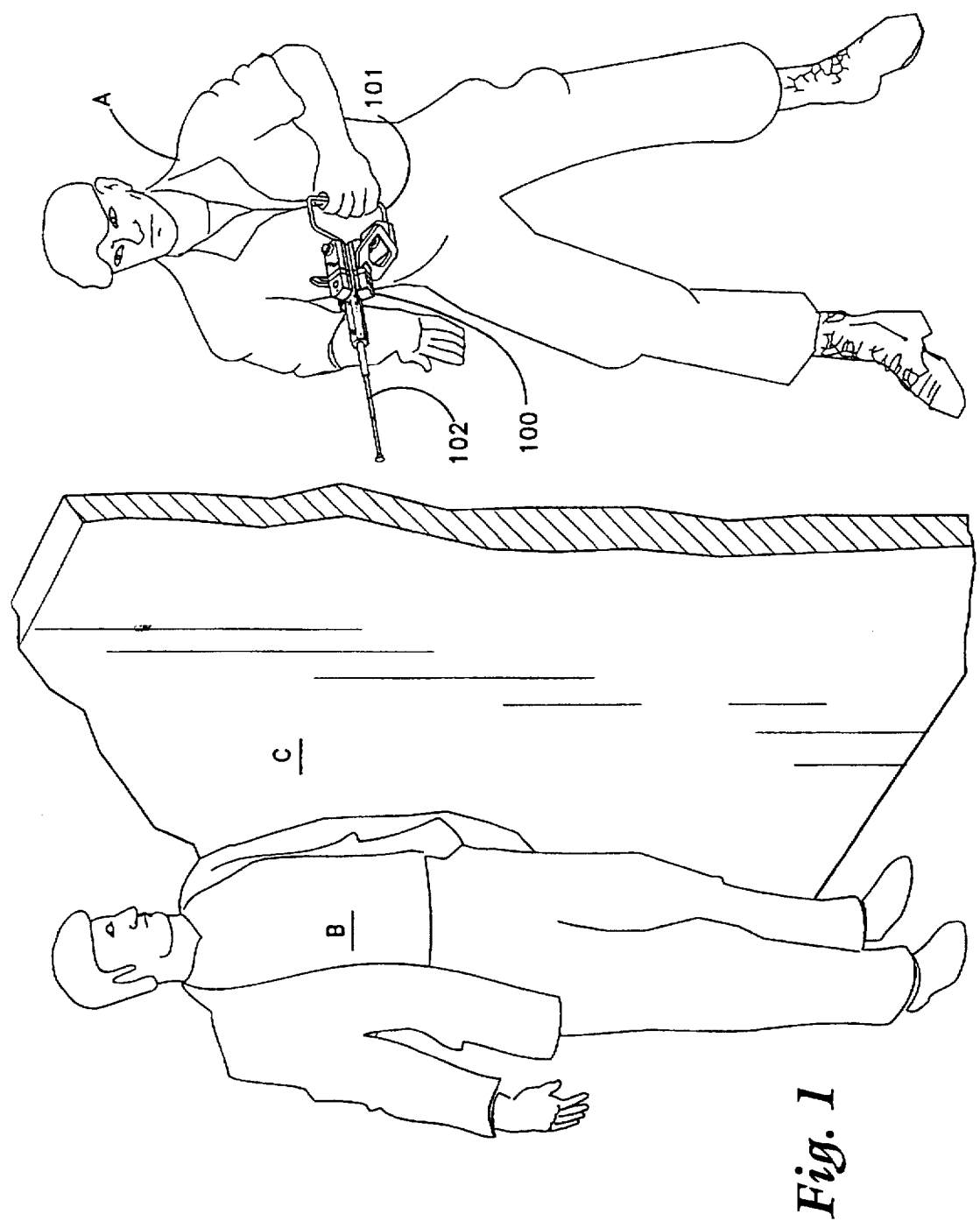
FIG. 1 is an environmental view of the locating device being used by a first person to locate a second, hidden person in accordance with the present invention.

The device according to the present invention is shown as locator device 100 in FIG. 1. A human operator A is shown using the locator device to detect the presence of a second human being B who is visually obscured behind a wall C. The handle 101 of the locator 100 is in electrical contact with the operator's hand, and the antenna 102 and the locator device's other component parts are acted on by the aforementioned forces. By holding the locator 100 in a horizontal level position and scanning the locator device 100 in a uniform and constant motion back and forth, the operator A detects a self-correcting constant-direction-seeking force, and the subsequent resulting torque upon the antenna 102 and the locator device's other component parts cause the locator device to point toward the direction and location of the visually obscured second human being B.

Figure 2:
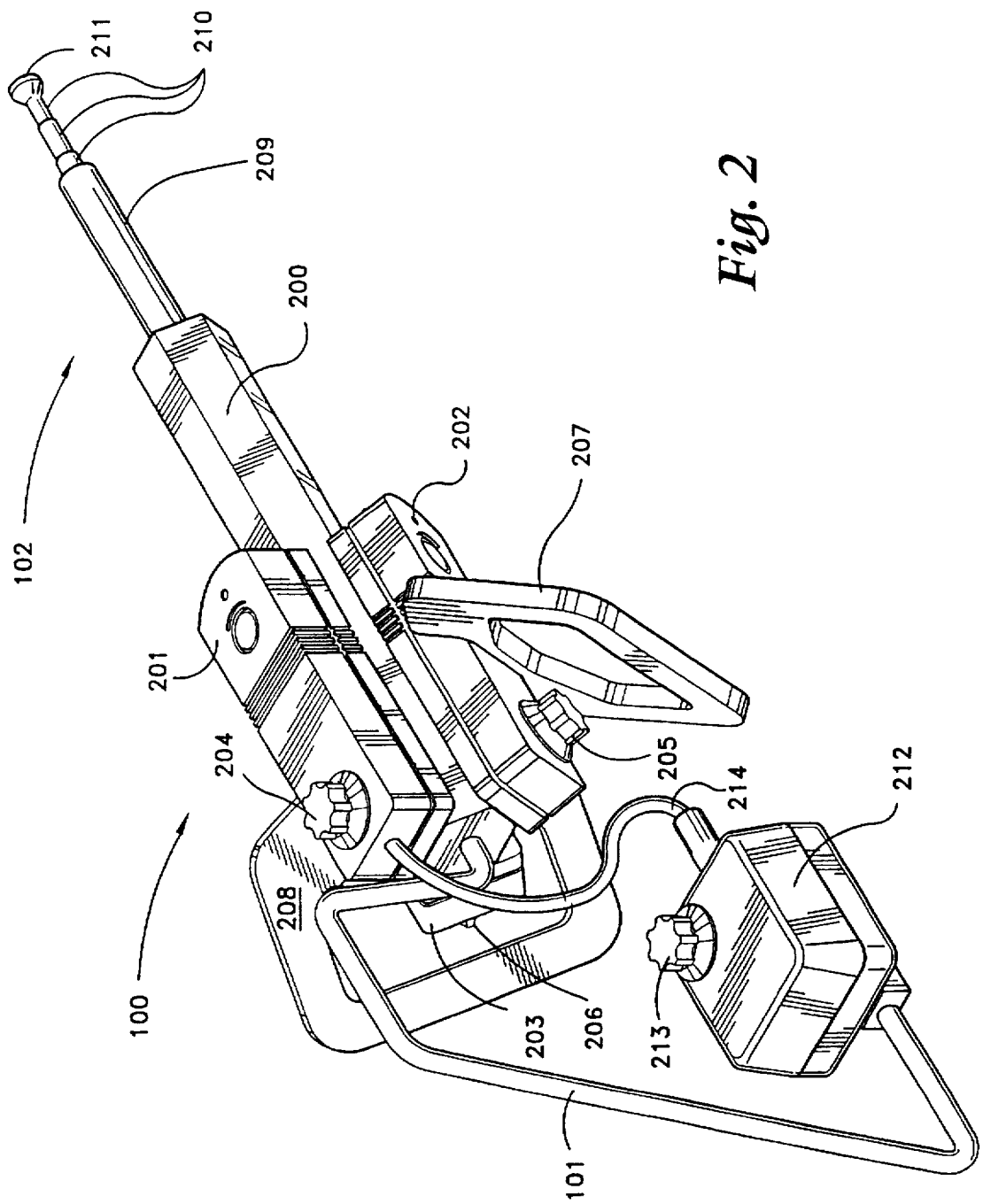
FIG. 2 is a perspective view of the locating device in accordance with the present invention.
Figure 3:
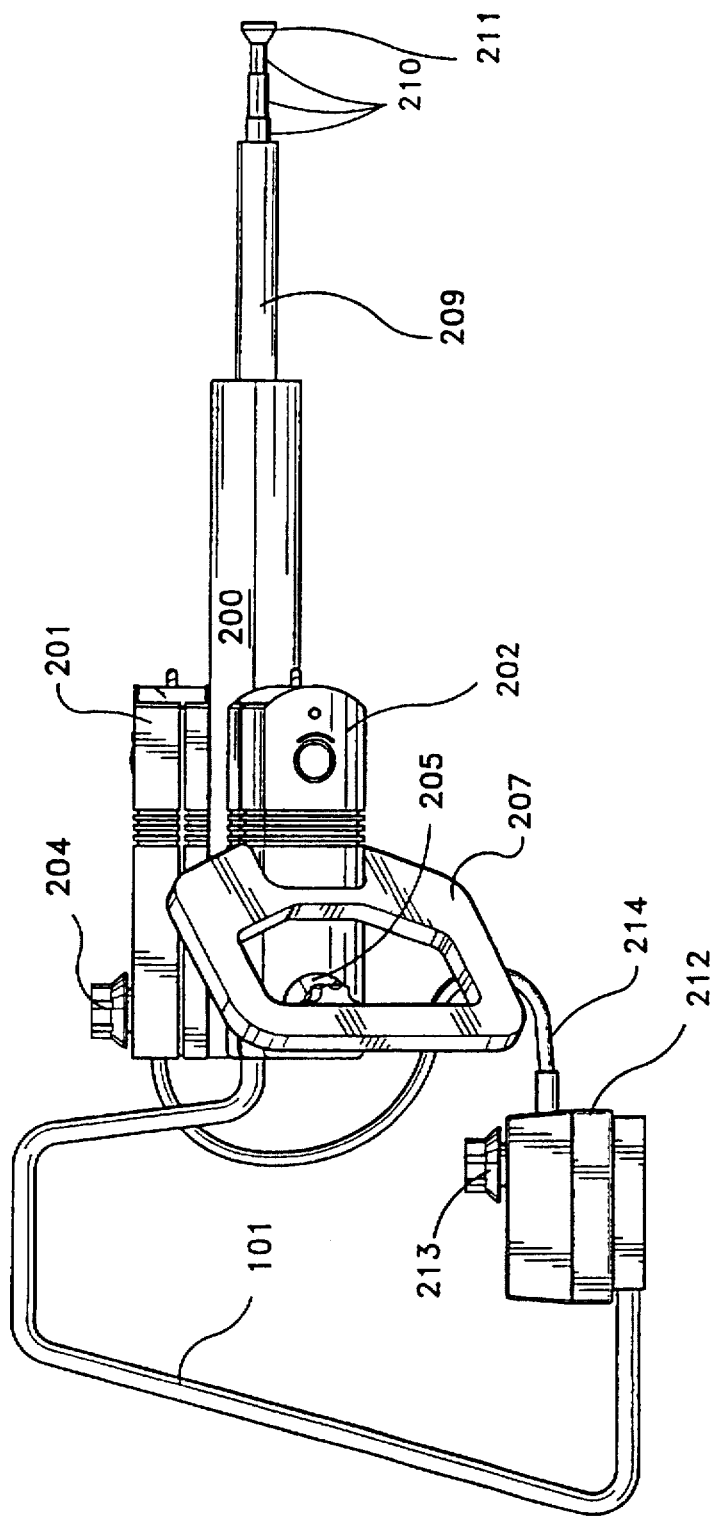
FIG. 3 is a right side view of the locating device shown in FIG. 2.
Figure 4:
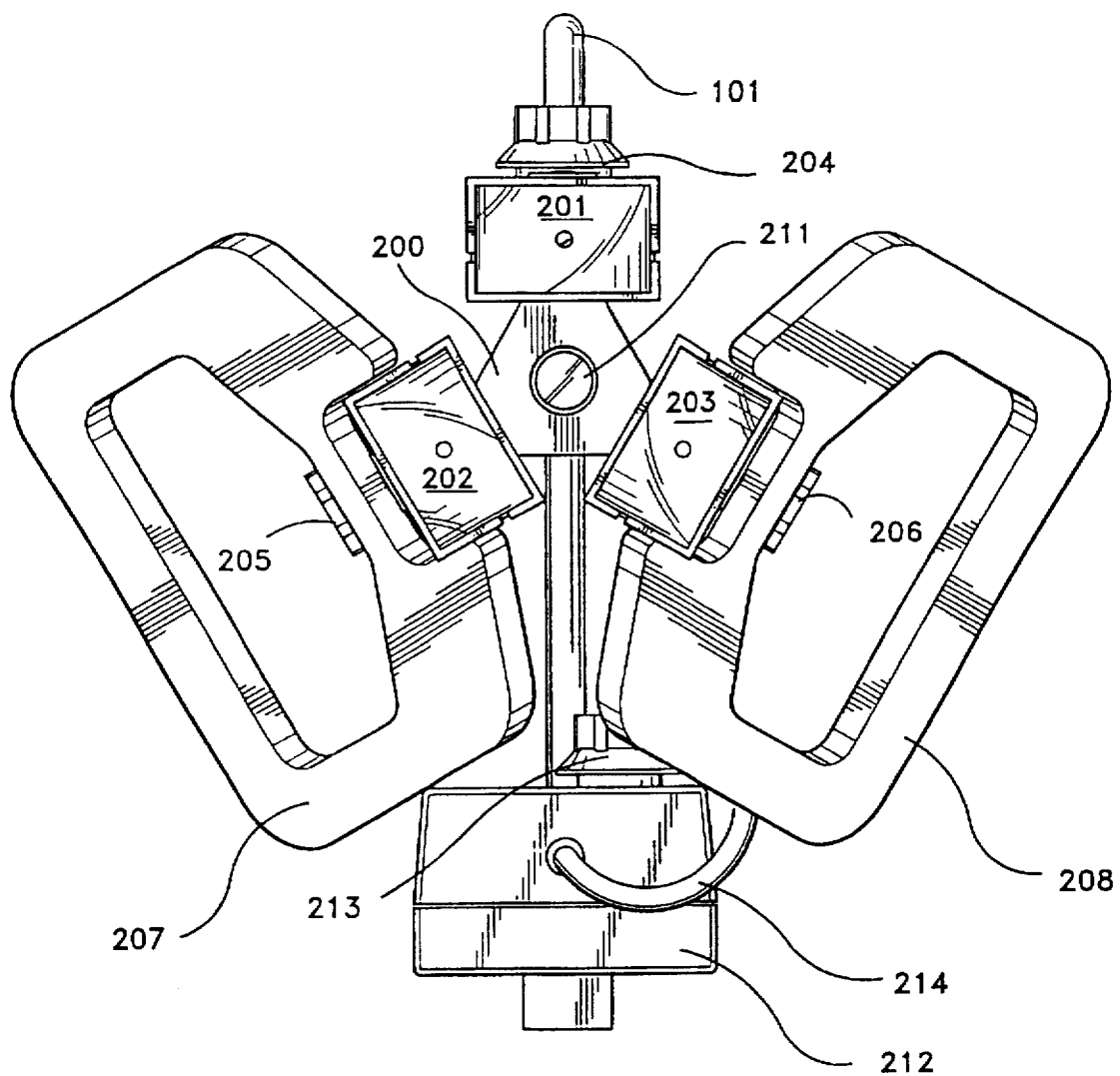
FIG. 4 is a front view of the locating device shown in FIG. 2.

The details of the exterior of the locator 100 can be seen in FIGS. 2–4. The antenna 102 includes a rear portion 209 made of nylon or similar material, telescoping sections 210, and an end knob 211. The antenna 102 protrudes from a central dielectric housing 200 in a coaxial arrangement. It is important to note that antenna 102 does not necessarily have to be of the telescoping type, and can be a one piece rigid or flexible type antenna. Furthermore, as all of the components of the locator device 100 effectively act as an antenna, the locating device operates as described without the antenna 102 installed, although the forces produced are greatly reduced.

Attached to the central dielectric housing 200 are three modules 201, 202, 203. The top module 201 is mounted directly over the common axis of the antenna 102 and the central dielectric housing 200 and in line with this axis. The lower right module 202 and lower left module 203 are spaced 120° apart from each other and the top module 201 and are also in line with the axis. Each module 201, 202 and 203 has a variable resistor control knob 204, 205 and 206, respectively. The lower right module 202 and lower left module 203 include parabolic antennas 207 and 208, respectively, both of the parabolic antennas being attached to their respective module in a swept back position. The handle 101 is formed from a metal rod that protrudes coaxially from the central dielectric housing 200. The handle 101 bends upward, extends horizontally for a short distance, bends downward to form a handle, and then bends forward to provide a support for a bottom tuning module 212. The bottom tuning module 212 includes a variable resistor control knob 213 and a cable 214 that attaches to the top module 201.

Figure 5:
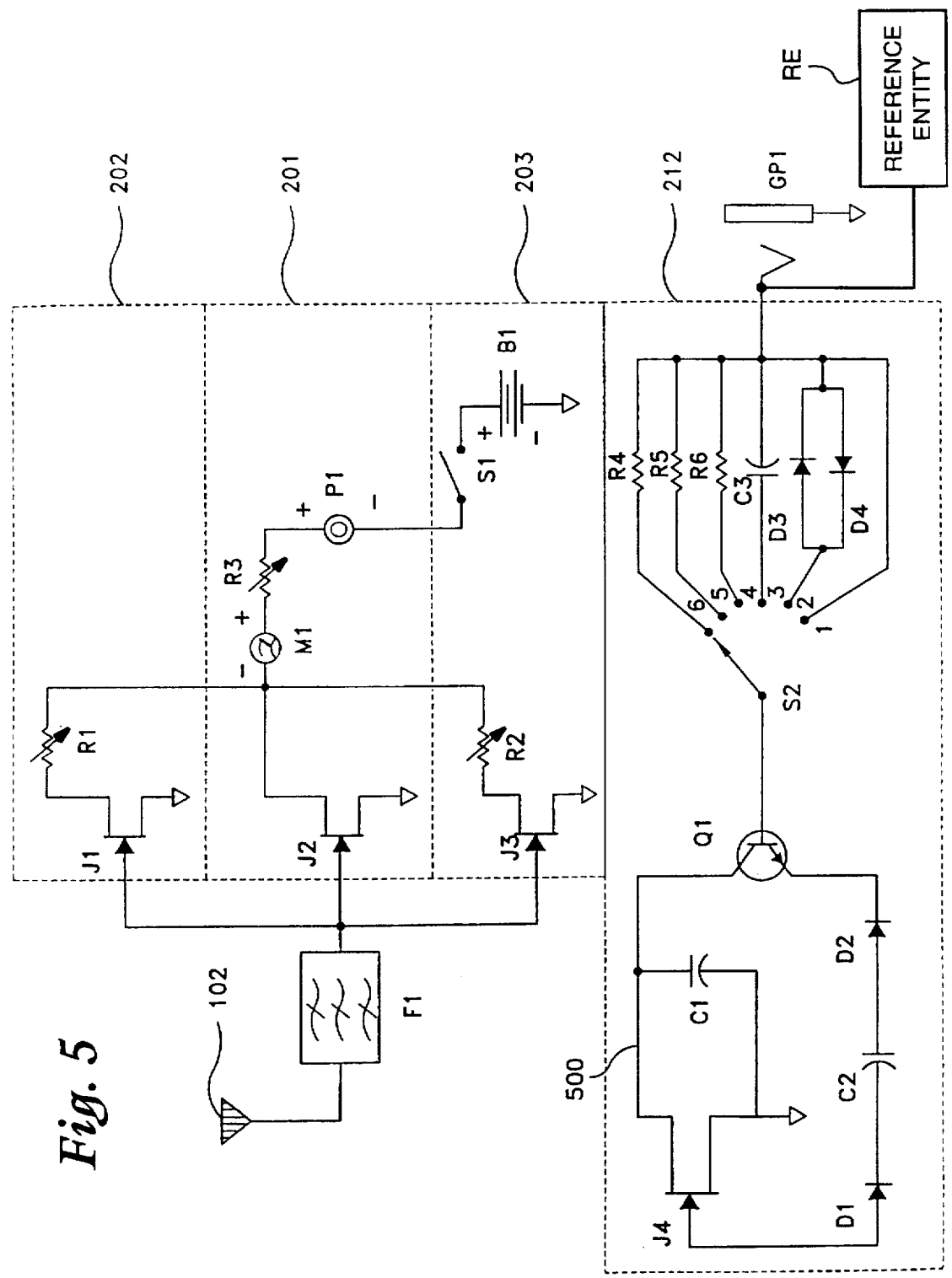
FIG. 5 is a schematic diagram of the three main modules and the bottom tuning module of the locating device of FIG. 2.

The electronic circuitry for the locator device 100 is shown in FIG. 5. The antenna 102 is connected to an optimal low pass filter F1, which removes all high frequency signals and noise from all external electromagnetic sources, including those from the human operator A himself. The details of the electronic circuitry and the geometrical design and materials of construction used in the locator device 100 are chosen so as to tailor the locator device 100 for a predetermined entity type. The output from the optimal low-pass filter F1 is fed to the gate of the three N-channel field effect transistors, FETs. The three FETs act as amplifiers and are housed one each in the three modules. The lower right module 202 contains FET J1 and a 0–100 kΩ variable resistor R1, the top module 201 contains FET J2, a DC ammeter M1, a 0–100 kΩ variable resistor R3, and a piezo buzzer P1, and the lower left module 203 contains FET J3, a 0–100 kΩ variable resistor R2, an on/off switch S1 and a 9-volt battery B1.

Variable resistors R1 and R2 adjust the current gain of FETs J1 and J3, respectively. By adjusting the gain of these FETs, the effective electrostatic effect on these devices is balanced relative to FET J2. The overall gain of FETs J1, J2 and J3, is adjusted by 0–100 kΩ variable resistor R3. The DC ammeter M1 is provided to indicate the combined current flow through all three FETs. In addition, the piezo buzzer P1 provides an audio output whose frequency increases as the current through the circuit increases. The battery B1 provides the required supply voltage (preferably nine volts) to operate the circuit, and the switch S1 provides a means for turning the amplifiers J1–J3 on and off.

The bottom module 212 contains the necessary circuitry for increasing the human operator's electrical parameter decay (RC) time constant, from μ seconds as occurs naturally to seconds as explained previously, needed to capture and lock onto the dielectrophoretic force exhibited by a target entity and the subsequent resulting torque, acceleration, vibration or any other measurable, quantifiable manifestation of the force detected by the locator device 100. A ⅛ inch grounding jack GP1 is used to provide a ground to the circuit by inserting a mating shorting plug into jack GP1. Once inserted, the mating plug (via jack GP1) provides a ground potential via the reference entity RE to each of 3.3 kΩ resistor R4, 22 kΩ resistor R5, 100 kΩ resistor R6, 0.01 mF capacitor C3, clipping diodes D3 and D4, and position one of a six-position selector switch S2. The six-position selector switch S2 can be moved to one of six-positions to connect the base of an NPN transistor Q1 to one of the above components. The NPN transistor Q1 makes up part of a tunable circuit that also includes an N-channel FET J4, a first 0.01 µF capacitor C1, a first diode D1, a second diode D2, an electrical line 500, and a second 0.01 µF capacitor C2. By inserting or removing the shorting plug into jack GP1 and changing the position of the switch S2, the gain of the transistor Q1 can be adjusted, and the overall frequency response of the tuned circuit in the bottom module 212 can be changed for maximum response.

As stated earlier, all of the components of FIG. 5 act as antenna extensions that increase the dielectrophoretic force and the subsequent resulting torque that is detected by the locator device 100. Every human being, as a locator device operator, has a different capacitance (C) and resistance (R) resulting in a low exponential decay time constant (=RC) for capturing and locking onto the dielectrophoretic force and the subsequent resulting torque. By adjusting R1–R3 and S2, the individual human operator and the locator device 100 can be jointly tuned and optimized to detect the maximum dielectrophoretic force and subsequent resulting torque for the specific human being operating the locator device 100. This is accomplished by using a reference entity (such as a visible human being) and adjusting S2 and R3 until the maximum dielectrophoretic force and subsequent resulting torque are detected by the individual human operator. Once the position of S2 has been determined, the operator notes the direction the antenna is pulled relative to the reference entity. If this direction is not exactly toward the reference, R1 and R2 are adjusted until the torque on the locator device 100 tends to point the antenna 102 directly toward the reference entity. After the locator device 100 is tuned and optimized, unobserved entities of the same type as the reference entity (e.g., humans, different species of animals, various precious and non-precious metals, plastics, and other materials) can be easily located by the device.

Figure 6:
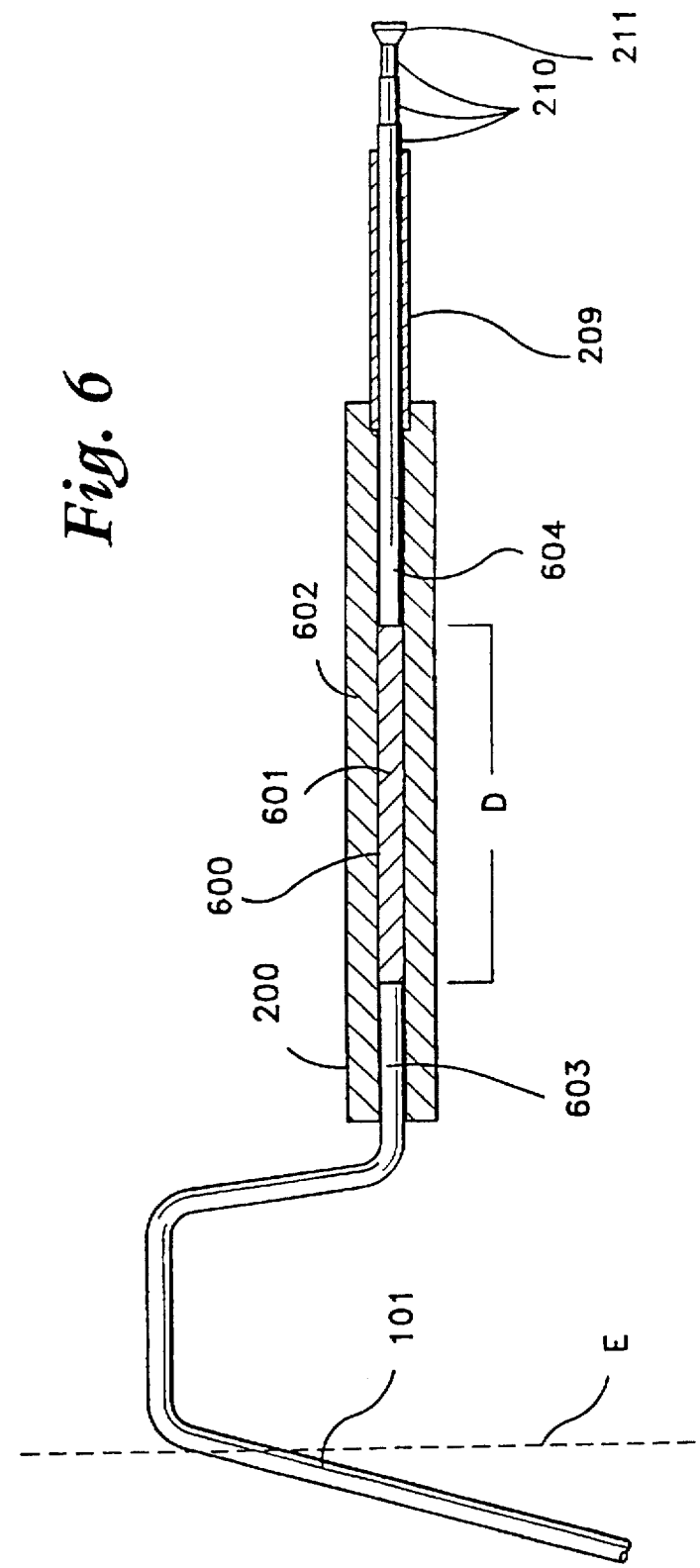
FIG. 6 is a cross-sectional view along the length and through the center of the locating device of FIG. 2.

The interior of the central dielectric housing 200 is shown in FIG. 6. One end 604 of the telescoping antenna 102 extends into the front end of the housing 200, while an end 603 of the handle 101 extends into the rear end of the housing 200. A cavity 600 is filed with a first dielectric material 601 that surrounds both the interior end 604 of the telescoping antenna 102 as well as the interior end 603 of the handle 101. Around this cavity 600 is a second dielectric material 602 that defines the shape of the cavity 600 and also contacts the interior end 604 of the telescoping antenna 102 as well as the interior end 603 of the handle 101 near the point where end 604 and end 603 exit the housing 200. The device's handle 101 with the operator's hand defines a pivot line E around which the dielectrophoretic force produces the subsequent resulting torque, acceleration, vibration or any other measurable, quantifiable manifestation of the force. The ends 604 and 603 are separated by a distance D, which distance is human-operator-specific and also affects the overall sensitivity and response of the locator device 100 as to maximum detectable force and torque.

While the specific dielectric materials for maximizing the torque effect on the antenna for different entities are still being researched, dielectrics have been found that produce a usable torque for precisely locating human beings. In particular, the handle 101 and the antenna 102 are preferably made of metal, material 601 is air, material 602 is PVC, and the rear portion 209 of the antenna is nylon. In addition, the circuitry in modules 201, 202, 203 and bottom module 212 is encapsulated in PVC, while the modules themselves, housing 200, as well as the parabolic antennas 207 and 208, are also made of PCV. When these materials are used, an effective dielectrophoretic force and the subsequent resulting torque are detected by the antenna 102 and the device's other component parts to precisely locate the presence of human beings. Dielectric material 601 may alternately be selected from the following materials with varying levels of resulting torque: water (distilled, deionized), glycerol, (di) ethylene, triethylene glycol, 2-ethyl-1,3-hexanediol, γ-butyrolactone, dimethylpropionamide, dimethyl sulfoxide, methanol, ethanol, propanol, barium titanate, lead titanate, and lead zirconate titanate.

Figure 7:
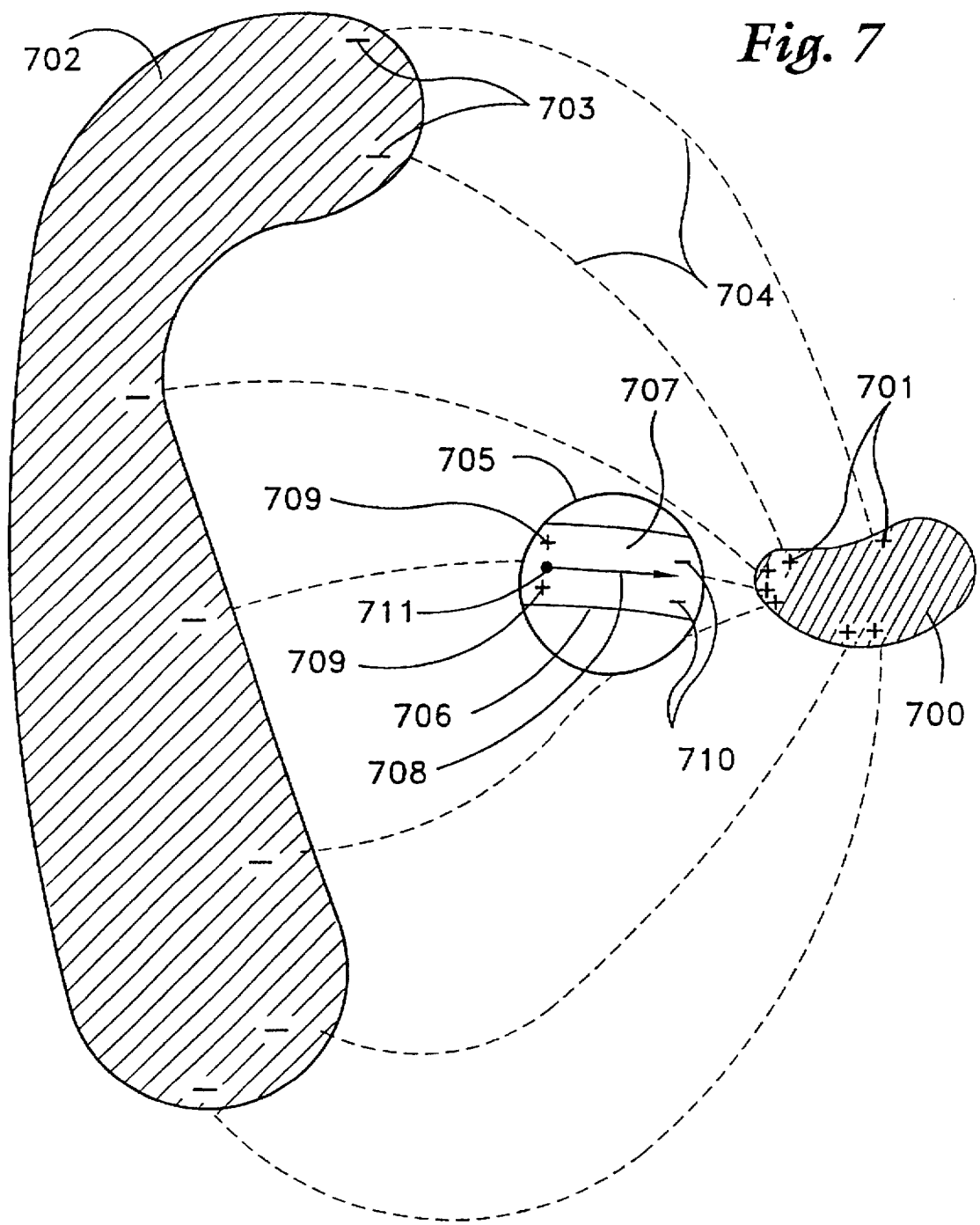
FIG. 7 is a schematic drawing of an entity, a ground plane, the device of the present invention and the entity's polarization electric field lines.

FIG. 7 shows a target entity of interest 700 and a surrounding ground plane 702. The entity's polarization charges 701 produce non-uniform electric field lines 704 that have a unique spatial pattern as shown. The non-uniform electric field lines 704 also have a unique spatial gradient pattern (not shown). The non-uniform electric field lines 704 terminate on the surrounding ground plane 702 and induce opposite polarization charges 703 thereon. An initially neutral matter or medium 705, such as the device of the present invention, is shown amidst the non-uniform electric field lines. The neutral matter 705 includes a cavity 706 filled with a specific dielectric material 707. The non-uniform electric field lines induce polarization charges 709 and 710 in the dielectric material 707. The neutral matter 705 also contains protuberant antennas 708 that are formed from a specific dielectric material and are in direct contact with the cavity 706 and the dielectric material 707. The protuberant antennas 708 form a pivot line 711 that is perpendicular to the plane containing FIG. 7. The dielectrophoretic force manifests itself as an easily detected torque motion of the antenna 708 about the pivot line 711.

It is to be understood that the present invention is not limited to the embodiments described above, but encompasses any and all embodiments within the scope of the following claims.

I claim:

1. A device for locating an entity of a predetermined type, said device comprising:

a housing having an interior with a first dielectric material therein; and a sinuous rod forming a handle, said rod having a first end extending from said interior of said housing and out a rear end of said housing, wherein said housing and said handle are constructed such that said device reacts to a unique non-uniform electric field squared spatial gradient three-dimensional pattern exhibited by said entity to produce a dielectrophoretic force and a quantifiable manifestation of said force on said device that indicates a specific direction relative to said entity.

2. The device according to claim 1, wherein:

said housing includes a cavity within said first dielectric material, said cavity being filled with a second dielectric material.

3. The device according to claim 2, further comprising:

an elongated antenna having a first end;

said elongated antenna's first end extending from said interior of said housing and out a front end of said housing.

4. The device according to claim 3, wherein:

said first and said second dielectric materials are both disposed in contact with said first end of said elongated antenna and said first end of said sinuous rod.

5. The device according to claim 2, further comprising at least a first module attached to a corresponding first surface of said housing, said first module housing a corresponding third dielectric material therein.

6. The device according to claim 5, wherein said first module has a corresponding first amplifier therein.

7. The device according to claim 5, comprising first, second and third modules attached to corresponding first, second and third surfaces of said housing, said modules housing corresponding third, fourth and fifth dielectric materials therein, respectively.

8. The device according to claim 7, wherein:

said first, second, third, fourth, and fifth dielectric materials are selected to maximize said dielectrophoretic force for said predetermined type of entity.

9. The device according to claim 7, wherein:

said sinuous rod includes a second end having a rear module mounted thereon.

10. The device according to claim 9, wherein:

said rear module on said rod has a sixth dielectric material therein.

11. The device according to claim 10, wherein:

said predetermined type of entity is a human;

said first, third, fourth, fifth and sixth dielectric materials are PVC; and said second dielectric material is selected from the group consisting of: air; water; glycerol; (di)ethylene; triethylene glycol; 2-ethyl-1,3-hexanediol; γ-butyrolactone; dimethylpropionamide; di-methyl sulfoxide; methanol; ethanol; propanol; barium titanate; lead titanate; and lead zirconate titanate.

12. The device according to claim 11, wherein:

said second dielectric material is air.

13. The device according to claim 10, further comprising:

an amplifier disposed in said rear module, said amplifier having an input;

a multi-position switch electrically connected to said input; and a plurality of tuning circuits coupled via said multi-position switch to said input.

14. The device according to claim 13, wherein:

said first module comprises a corresponding first variable resistor therein for changing the gain of said first amplifier.

15. The device according to claim 7, wherein said modules are disposed radially 120 degrees from one another.

16. The device according to claim 7, wherein said first, second and third modules comprise first, second and third amplifiers therein, respectively.

17. The device according to claim 16, further comprising an elongated antenna having a first end, said first end extending from said interior of said housing and out a front end of said housing, wherein said first module and said second module each have a parabolic antenna mounted thereon in a swept back position.

18. The device according to claim 17, wherein:

said right bottom module and said left bottom module each have a parabolic antenna mounted thereon in a swept back position.

19. The device according to claim 16, wherein said first module comprises a first variable resistor therein coupled with said first, second and third amplifiers, said variable resistor changing a gain of said first, second and third amplifiers.

20. The device according to claim 19, wherein said second module comprises a second variable resistor coupled with said second amplifier and said third module comprises a third variable resistor coupled with said third amplifier, said second and third variable resistors changing a gain of said second and third amplifiers, respectively.

21. The device according to claim 16, wherein said second dielectric material is air.

22. The device according to claim 5, wherein said predetermined type of entity is a human, and wherein said first and third dielectric materials are PVC and said second dielectric material is selected from the group consisting essentially of: air, water, glycerol, (di)ethylene, triethylene glycol, 2-ethyl-1,3-hexanediol, γ-butyrolactone, dimethylpropionamide, di-methyl sulfoxide, methanol, ethanol, propanol, barium titanate, lead titanate, and lead zirconate titanate.

23. A method for locating an entity of a predetermined type, said method comprising:

providing a locating device having a housing and a handle;

holding said locating device by said handle;

scanning said locating device in a constant uniform motion back and forth in a general direction toward said entity; and observing a reaction of said device caused by a quantifiable manifestation of a dielectrophoretic force produced by an interaction between said device and a unique non-uniform electric field squared spatial gradient three-dimensional pattern exhibited by said entity, to determine a specific direction relative to said entity.

24. The method according to claim 23, said method further comprising:

providing said locating device with at least one dielectric material; and wherein said at least one dielectric material is preselected depending on said predetermined type of entity.

25. The method according to claim 24, said method further comprising:

providing said locating device with at least two dielectric materials;

a first of said dielectric materials being PVC;

a second of said dielectric materials being selected from the group consisting of: air; water (distilled, deionized); glycerol; (di)ethylene; triethylene glycol; 2-ethyl-1,3-hexanediol; γ-butyrolactone; dimethylpropionamide; di-methyl sulfoxide; methanol; ethanol; propanol; barium titanate; lead titanate; and lead zirconate titanate.

26. A device for detecting a unique non-uniform electric field squared spatial gradient three-dimensional pattern, the device comprising:

a housing defining a cavity therein;

a first dielectric material disposed in said housing; and a handle formed of a conductive material disposed in contact with said first dielectric material, wherein said housing and said handle are constructed such that said device reacts to the unique non-uniform electric field squared spatial gradient three-dimensional pattern to produce a dielectrophoretic force and a quantifiable manifestation of said force on said device.

27. The device according to claim 26, further comprising an antenna disposed in operative communication with said housing.

28. The device according to claim 27, wherein said antenna is defined by the device components.

29. The device according to claim 27, wherein said antenna is formed of a conductive material and is disposed in contact with said first dielectric material.

30. The device according to claim 29, wherein said housing comprises a front end and a rear end, said antenna being secured to said housing at said front end and said handle being secured to said housing at said rear end.

* * * * *